United States Patent
Lai et al.

(10) Patent No.: US 10,383,531 B2
(45) Date of Patent: Aug. 20, 2019

(54) PHYSIOLOGICAL SIGNALS MEASUREMENT SYSTEMS AND METHODS THEREOF

(71) Applicant: Wistron Corp., New Taipei (TW)

(72) Inventors: Yu-Ren Lai, New Taipei (TW); Yu-Yen Chen, New Taipei (TW)

(73) Assignee: WISTRON CORP., New Taipei (TW)

( * ) Notice: Subject to any disclaimer, the term of this patent is extended or adjusted under 35 U.S.C. 154(b) by 106 days.

(21) Appl. No.: 15/847,800

(22) Filed: Dec. 19, 2017

(65) Prior Publication Data

US 2019/0046057 A1 Feb. 14, 2019

(30) Foreign Application Priority Data

Aug. 9, 2017 (TW) .............................. 106126879 A (51) Int. Cl.
*A61B 5/024* (2006.01)
*G06T 7/00* (2017.01)
(Continued)

(52) U.S. Cl.
CPC ........ *A61B 5/02416* (2013.01); *A61B 5/7203* (2013.01); *A61B 5/7278* (2013.01);
(Continued)

(58) Field of Classification Search
CPC . A61B 5/0205; A61B 5/02416; A61B 5/0077; A61B 5/024; A61B 5/7203;
(Continued)

(56) References Cited

U.S. PATENT DOCUMENTS

2014/0180132 A1* 6/2014 Shan .................... A61B 5/0059
600/476
2014/0275832 A1* 9/2014 Muehlsteff ........... A61B 5/0205
600/301
(Continued)

OTHER PUBLICATIONS

Wim Verkruysse et al., "Remote Plethysmographic Imaging Using Ambient Light," Optics Express, Dec. 2008, pp. 21434-21445, vol. 16, No. 26, Optical Society of America, US.
Mayank Kumar et al., "DistancePPG: Robust Non-contact Vital Signs Monitoring Using a Camera," Biomedical Optics Express, May 2015, pp. 1565-1588, vol. 6, No. 5, Optical Society of America, US.

*Primary Examiner* — Jingge Wu (57) ABSTRACT

A method for measuring a physiological signal is provided, including the steps of: receiving a video and performing face detection for each image frame thereof; performing photo-plethysmography (PPG) calculation and analysis on first face image for first image frame to obtain first PPG information of first regions and second PPG information of corresponding second regions; determining at least one region-of-interest (ROI) and one noise reference region according to the first PPG information and the second PPG information; generating ROI information and noise reference region information based on the ROI and the noise reference region; and performing the PPG calculation and analysis on the ROI and the noise reference region of the second face image of each subsequent second image frame and generating corresponding third PPG information; and counting the PPG information of all the image frames to calculate a measured value of a physiological signal.

14 Claims, 10 Drawing Sheets

(51) Int. Cl.
  *G06K 9/00* (2006.01)
  *A61B 5/00* (2006.01)
(52) U.S. Cl.
  CPC ........ *G06K 9/00228* (2013.01); *G06T 7/0012* (2013.01); *G06T 2207/10016* (2013.01); *G06T 2207/30104* (2013.01); *G06T 2207/30201* (2013.01)
(58) Field of Classification Search
  CPC .............. A61B 5/02405; A61B 5/7207; G06T 2207/10016; G06T 7/0016; G06T 7/0012; G06T 2207/30101; G06K 9/00228; G06K 2009/00939
  See application file for complete search history.

(56) References Cited

U.S. PATENT DOCUMENTS

| | | | | |
|---|---|---|---|---|
| 2014/0303454 | A1* | 10/2014 | Clifton | A61B 5/0205 600/301 |
| 2016/0253820 | A1* | 9/2016 | Jeanne | A61B 5/7207 382/107 |
| 2017/0164904 | A1* | 6/2017 | Kirenko | A61B 5/7214 |
| 2017/0238842 | A1* | 8/2017 | Jacquel | A61B 5/743 |
| 2017/0325686 | A9* | 11/2017 | Shan | A61B 5/0059 |
| 2018/0042486 | A1* | 2/2018 | Yoshizawa | A61B 5/0013 |
| 2018/0153455 | A1* | 6/2018 | Guazzi | A61B 5/0077 |
| 2018/0360387 | A1* | 12/2018 | Bulut | A61B 5/6886 |

\* cited by examiner

PHYSIOLOGICAL SIGNALS MEASUREMENT SYSTEMS AND METHODS THEREOF

CROSS REFERENCE TO RELATED APPLICATIONS

This Application claims priority of Taiwan Application No. 106126879, filed on Aug. 9, 2017, and the entirety of which is incorporated by reference herein.

BACKGROUND OF THE INVENTION

Field of the Invention

The invention generally relates to image processing systems and methods, and more particularly, to systems and methods for measuring physiological signals.

Description of the Related Art

Image-based pulse detection is an emerging technology in recent years. This technology features the advantage of pulse detection conduction through common commercially available video cameras. It is a non-contact technology involving no direct contact between the subject's face and the sensor (video camera). Thus, it is without health concerns other traditional contact finger-type pulse detectors have. A common type of non-contact image heart rate and pulse detection method involves extracting three color frequencies, namely red (R), green (G), and blue (B). Based on the Photoplethysmography (PPG) of the respective color frequencies, the heart beat frequency (heart rate) or pulse is calculated. PPG signals are signals detected by recording light changes in blood flow pulse changes in blood vessels through the principle of "light sensing components absorbing light energy". The blood flow per unit region will change with the heartbeat, while the light sensing components will change with blood flow changes and sensing voltage changes, through which the heart rate or pulse can be calculated. However, this calculation method targets the measurement and tally of the PPG of the entire face image. If the PPG of a certain part of the skin is not obvious, calculation results are likely affected.

Later, some improved non-contact image heart rate/pulse measurement methods have been proposed, which targets skin, brightness, and movement improvement. This method involves first locating the face from feature points, dividing the face into several regions, and defining track points in respective regions and tracking the entire region. Finally, they are further divided into numerous sub-regions to calculate the PPG average and find the part of the facial skin that best reflects the heart rate.

However, two problems are still encountered with the abovementioned improved non-contact image heart rate/pulse measurement method. First, the heart rate frequency detected using the above method may still be interfered by environmental light sources. This will result in inability to determine background noise intensity and denoise, thus affecting accuracy. In addition, the above method involves constant tracking of the locations of different regions, thus consuming considerable computing resources. In particular, for embedded systems with fewer computing resource and more limitations, the feature extraction tracking will slow down the overall computing speed.

BRIEF SUMMARY OF THE INVENTION

Physiological signal measurement systems and associated methods for measuring physiological signals are provided. In an exemplary embodiment, a method for measuring a physiological signal is provided. The method for measuring the physiological signal includes the steps of: receiving a video including a plurality of continuous image frames and performing face detection on each of the image frames to obtain a face image for each image frame, wherein the continuous image frames include a first image frame and a plurality of second image frames, and wherein the first image frame includes a first face image having first regions, each of the first regions having a plurality of second regions corresponding thereto; performing a photo-plethysmography (PPG) calculation and analysis on the first face image of the first image frame to obtain a plurality of first PPG information of the first regions and a plurality of second PPG information of corresponding second regions; determining a reserved region from the first regions according to the first PPG information of the first regions and a first threshold value, and determining at least one region-of-interest (ROI) and a noise reference region according to results of comparing the second PPG information of corresponding second regions for the reserved region and a second threshold value; generating an ROI information and a noise reference region information based on the at least one ROI and the noise reference region of the first face image, wherein the ROI information includes location information and the PPG information corresponding to the at least one ROI and the noise reference region information includes location information and the PPG information corresponding to the noise reference region; performing the PPG calculation and analysis on the ROI and the noise reference region of each second face image of each of the second image frames and generating corresponding third PPG information based on the ROI information and the noise reference region information; and counting the PPG information of all the image frames to calculate a measured value of the physiological signal.

Another exemplary embodiment of a physiological signal measurement system includes an image input device, an image processor and a display device. The image input device is configured to obtain a video including a plurality of continuous image frames, wherein the continuous image frames include a first image frame and a plurality of second image frames, and wherein the first image frame includes a first face image having first regions, each of the first regions having a plurality of second regions corresponding thereto. The image processor is coupled to the image input device and configured to receive the video and perform face detection on each of the image frames to obtain a face image for each image frame, perform a photo-plethysmography (PPG) calculation and analysis on the first face image of the first image frame to obtain a plurality of first PPG information of the first regions and a plurality of second PPG information of the corresponding second regions, determine a reserved region from the first regions according to the first PPG information of the first regions and a first threshold value, determines at least one region-of-interest (ROI) and a noise reference region according to results of comparing the second PPG information of corresponding second regions for the reserved region and a second threshold value, generate an ROI information and a noise reference region information based on the at least one ROI and the noise reference region of the first face image, wherein the ROI information includes location information and the PPG information corresponding to the at least one ROI and the noise reference region information includes location information and the PPG information corresponding to the noise reference region, perform the PPG calculation and analysis on the ROI and the noise reference region of each second face image of each of the second image frames and generate corresponding third PPG information based on the ROI information and the noise reference region information, and count the PPG information of all the image frames to calculate a measured value of a physiological signal. The display device is coupled to the image processor, configured to display the measured value of the physiological signal.

Methods disclosed above may be practiced by the disclosed apparatuses or systems which are hardware or firmware capable of performing particular functions and may take the form of program code embodied in a tangible media. When the program code is loaded into and executed by an electronic device, a processor, a computer or a machine, the electronic device, the processor, the computer or the machine becomes an apparatus for practicing the disclosed method.

BRIEF DESCRIPTION OF DRAWINGS

The invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims. It should be understood that the embodiments may be realized in software, hardware, firmware, or any combination thereof.

Embodiments of the invention provide systems for measuring physiological signals and methods thereof, which can through the non-contact physiological signal (such a heart rate) detection algorithm of the invention, directly find reliable locations in the image for detecting the heart rate and not waste computing resources to extract and track features from every image, and further utilize the regions with less obvious facial PPG changes to determine background noise for denoising, thus improving the measurement accuracy in one way and resolving the problem of bulk computing in the other.

Figure 1:
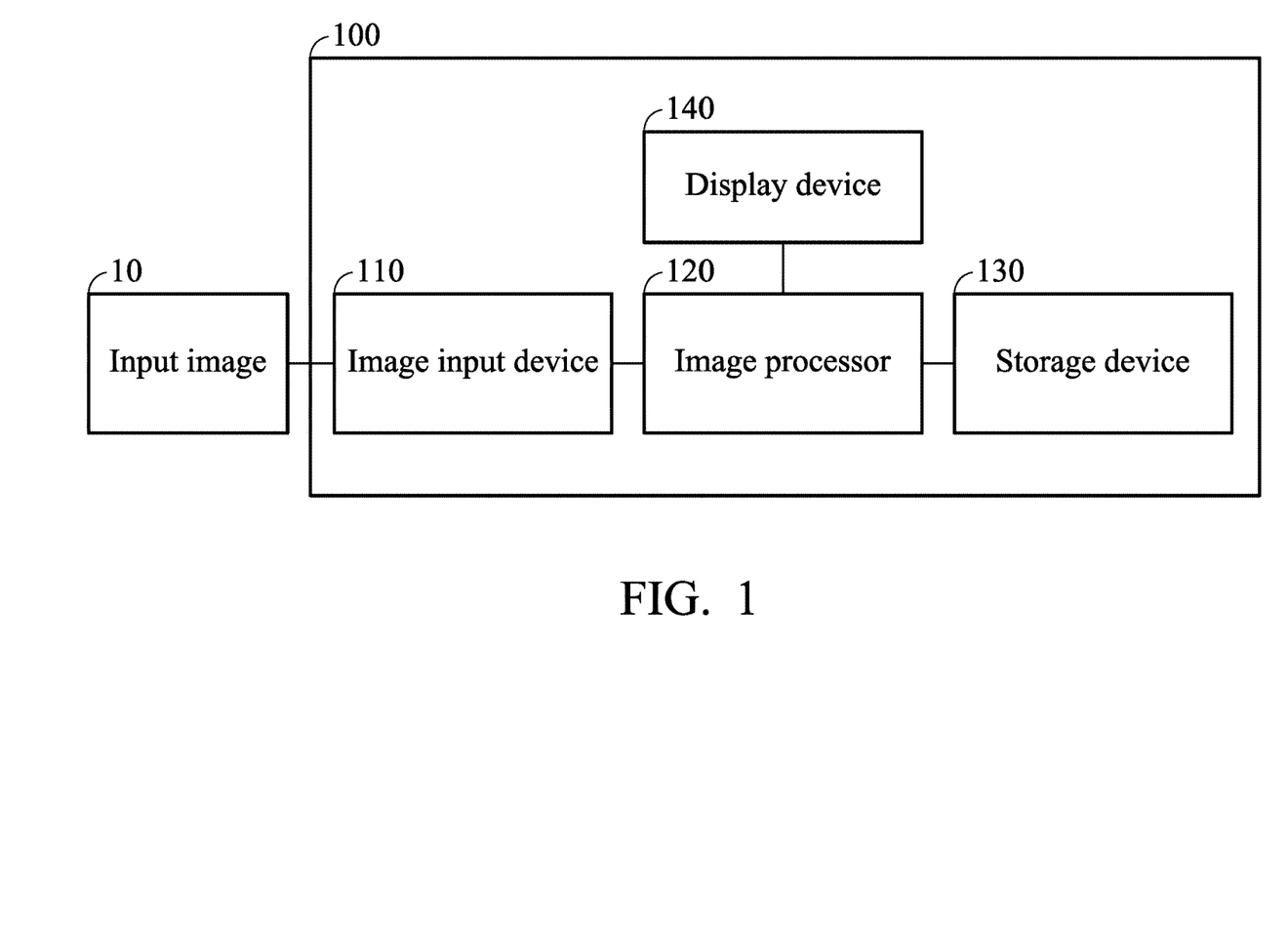
FIG. 1 is a schematic diagram illustrating an embodiment of an image data processing system of the invention.

FIG. 1 is a schematic diagram illustrating an embodiment of an image data processing system of the invention. As shown in FIG. 1, the image data processing system 100 includes at least an image input device 110, an image processor 120, a storage device 130, and a display device 140. The image input device 110 may be configured to receive or acquire an input image 10 and provide the input image 10 to the image processor 120 for subsequent image analyzing and processing. For example, the image data processing system 100 may be a laptop computer, a desktop computer, a tablet device, or other handheld device (e.g., a smartphone or a wearable device), but the invention is not limited thereto. For example, in an embodiment, the image input device 110 may be an image acquisition unit, such as one of an infrared image acquisition device, a Charge Coupled Device (CCD) element or Complementary Metal Oxide Semiconductor (CMOS) sensing element, or any combination thereof, and the invention is not limited thereto. In particular, the input image 10 can be defined as a video segment with a certain time length which is captured from the user who keeps no movement in front of the image input device 110, such as a camera, for a period of time. In other words, the input image 10 can be continuous images having a predetermined length of time, and each image includes a face region image.

The image processor 120 which is coupled to the image input device 110 and the storage device 130, that may be used to execute one or more types of computer-readable mediums stored within the storage devices 130 and execute instruction set and/or program codes to perform the method for measuring the physiological signal of the present invention based on the input image 10 provided by the image input device 110, which will be discussed further in the following paragraphs. The image processor 120 may be a Central Processing Unit (CPU), Micro-Control Unit (MCU), Graphics Processing Unit (GPU), Digital Signal Processor (DSP), or the like, which provides the function of image data analyzing, processing and computing. The storage device 130 may be a non-volatile storage medium (e.g., Read-Only Memory (ROM), Flash memory, magnetic tape, hard disk, or optical disc), or a volatile storage medium (e.g., Random Access Memory (RAM)), or any combination thereof for storing data, such as intermediate data generated during the calculation process and the processed result information and so on. In some embodiments, the storage device 130 may store the input image(s) 10 in advance, and the image processor 120 may directly access the input image(s) 10 from the storage device 130 for subsequent processing without passing through the image input device 110.

The storage device 130 may further store information about previously processed images, which may be used for subsequent physiological signal measurements. For example, the storage device 130 may store image coordinate values, pixel values, PPG values, and the like with respect to the region-of-interest (ROI). Thereafter, the image processor 120 may apply the stored information to perform measurement of physiological signals such as heart rate, pulse signals, and the like.

The display device 140 may be any device capable of displaying or presenting recognition results. The display device 140 may display related data, such as texts, figures, interfaces, and/or information such as displaying or presenting measurement results. The display device 140, such as a liquid crystal display (LCD) etc., may be configured to present an image of the measurement results (including any image format, such as bmp, jpg, png and other formats etc.) or display the results of the measurement. It could be understood that, in some embodiments, the display device 140 may be a screen integrated with a touch-sensitive device (not shown). The touch-sensitive device has a touch-sensitive surface comprising sensors in at least one dimension to detect contact and movement of at least one object (input tool), such as a pen/stylus or finger near or on the touch-sensitive surface. Therefore, users may be able to input commands or signals via the display device 140.

It could be understood that each of the elements or modules in the presented embodiments may be a device having a corresponding function, which may have the appropriate hardware circuits or elements to perform the corresponding function, however, the device is not limited to be entity device, which may also be a virtual device having program codes and software(s) with respective functions or a device having capabilities for processing and running the program codes and software(s). The manner of operations of the respective elements may further refer to the following description of the methods. Specifically, the physiological signal measurement system 100 may control the operations of the image input device 110, the storage device 130, and the display device 140 via the image processor 120 to perform the method of measuring the physiological signal of the invention. For ease of explanation, in the embodiments of the latter paragraphs, will use the physiological signal to be measured as a pulse signal as an example, for the purpose of illustrating possible embodiments of the invention. Those who are skilled in this technology may still make various alterations and modifications without departing from the scope and spirit of this invention.

Figure 2A:
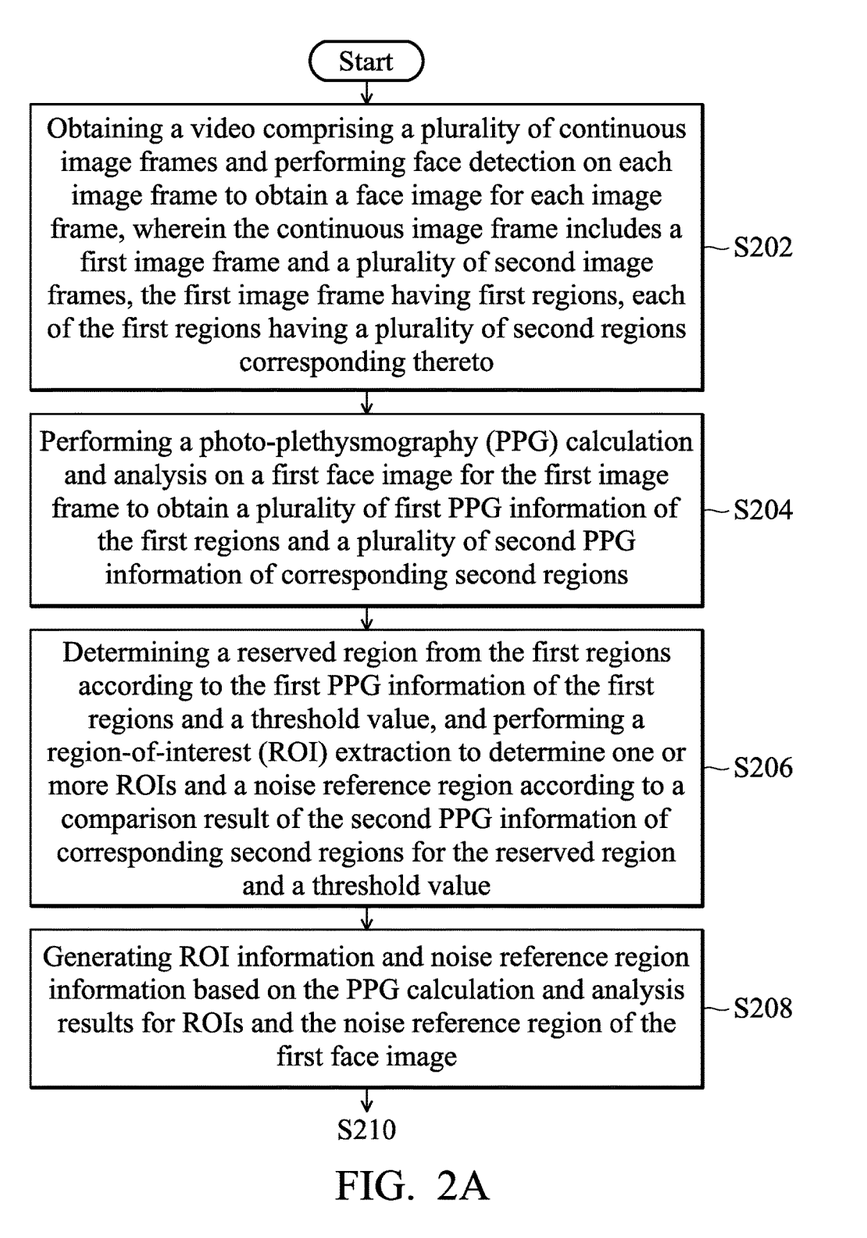
FIGS. 2A and 2B show a flowchart of an embodiment of a method for measuring the physiological signal of the invention.
Figure 2B:
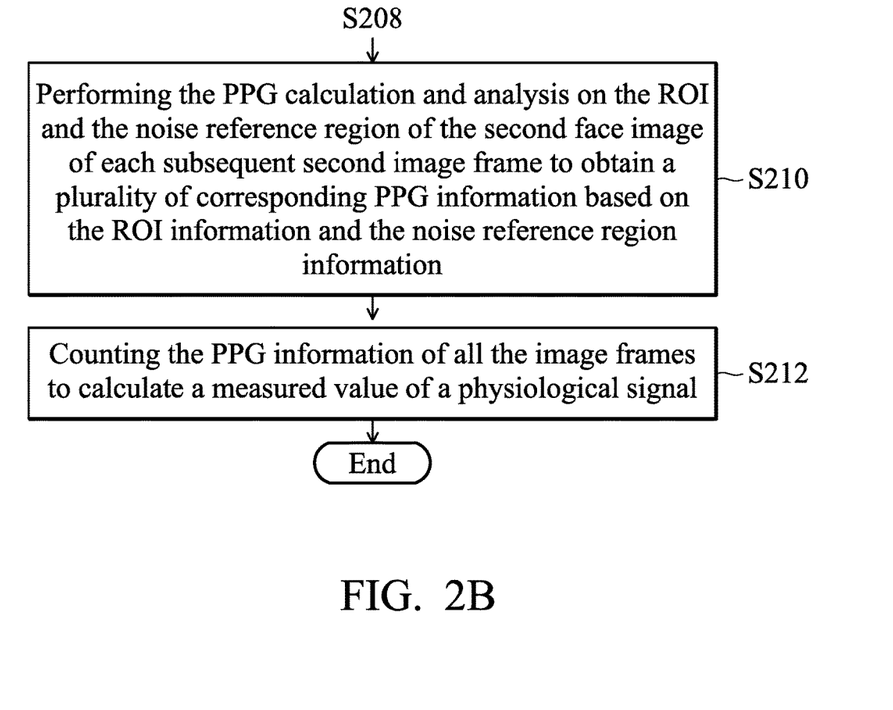

FIGS. 2A and 2B show a flowchart of an embodiment of a method for measuring the physiological signal of the invention. Please refer together with FIG. 1, FIG. 2A and FIG. 2B. The method of measuring a physiological signal in accordance with the embodiments of the invention may be applied to a physiological signal measurement system, for example, the physiological signal measurement system 100 as shown in FIG. 1, and the method may be performed by the image processor 120.

Figure 3A:
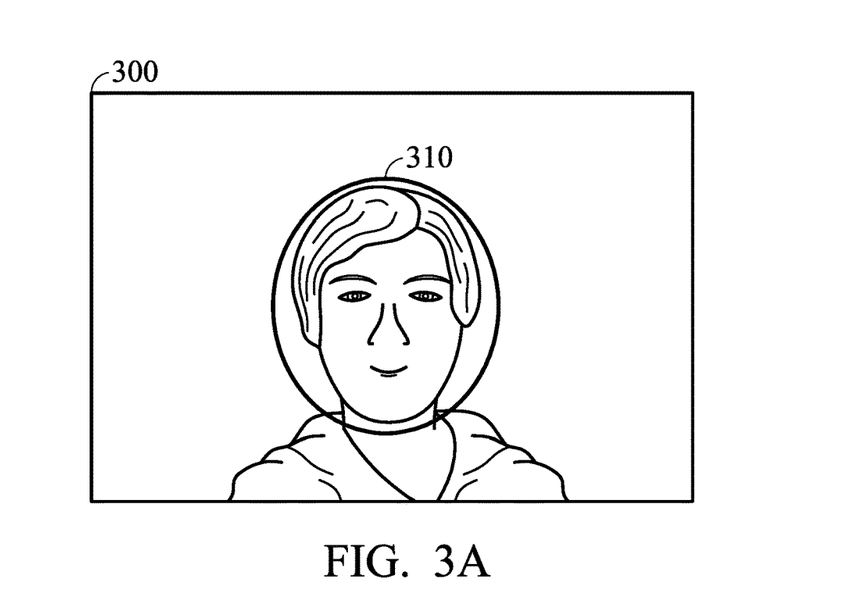
FIG. 3A is a schematic diagram illustrating an embodiment of a face detection result of the invention.

First, as shown in step S202, the image processor 120 receives a video including a plurality of continuous image frames and performs face detection on each image frame to obtain a face image for each image frame. The continuous image frame includes a first image frame and a plurality of second image frames. The first image frame may be the first image frame of the video while the second image frames are the remaining image frames subsequent to the first image frame. In this step, the video input device 110 may capture/obtain a video including a number of continuous image frames, and the image processor 120 may receive the video captured by the video input device 110 and perform face detection on each image frame to obtain the face image of each image frame. Specifically, when the user wants to perform heart rate and/or pulse signal measurement, the user must keep no movement in front of the camera lens for a period of time to cumulative shoot a certain length of the video (video segment) and sensing in the appropriate and adequate ambient light source. Therefore, entire video recorded by the user must be first inputted, and the number of image/video frames (i.e. the image/video frame number) to be processed may be defined and face detection can be performed based on the images of the video. It should be noted that details of specific face detection algorithms may be practiced by various face detection processing techniques which are well-known by those skilled in the art, and thus such details are omitted here for brevity. FIG. 3A is a schematic diagram illustrating an embodiment of a face detection result of the invention. As shown in FIG. 3A, image 310 is a face image of the image 300. In this embodiment, the first image frame includes a first face image, wherein the first face image has multiple first regions, each of the first regions having multiple second regions. In one embodiment, the image processor 120 may further perform rough skin segmentation on skin portion of the first face image according to face feature points to divide the first face image into the first regions. Each of the first regions may further be performed with a fine segmentation to subdivide into a number of smaller second regions. That is, each first region has a plurality of second region corresponding thereto.

Next, as shown in step S204, the image processor 120 performs a photo-plethysmography (PPG) calculation and analysis on the first face image for the first image frame to obtain a plurality of first PPG information of the first regions and a plurality of second PPG information of corresponding second regions, and then, as shown in step S206, determines a reserved region from the first regions according to the first PPG information of the first regions and a threshold value, and performs a region-of-interest (hereinafter referred to as ROI) extraction to determine one or more ROIs and a noise reference region according to results of comparing the second PPG information of corresponding second regions for the reserved region and a threshold value.

ROI represents a region where the PPG changes is obvious in the face image, and the noise reference region is a flat region with a small change in the face PPG. In some embodiments, the ROI extraction may comprise the steps of comparing the first PPG information of each of the first regions with the first threshold value and setting one of the first regions whose first PPG information is within a range of the first threshold value as the reserved region. In one embodiment, the step of determining the ROI and the noise reference region according to the results of comparing the second PPG information of corresponding second regions for the reserved region and the second threshold value may further comprise the step of comparing the second PPG information of each of the second regions with the second threshold value, setting one of the second regions whose second PPG information is within a range of the second threshold value as the ROI and determining the noise reference region from the second regions whose second PPG information are not within the range of the second threshold value.

Figure 3B:
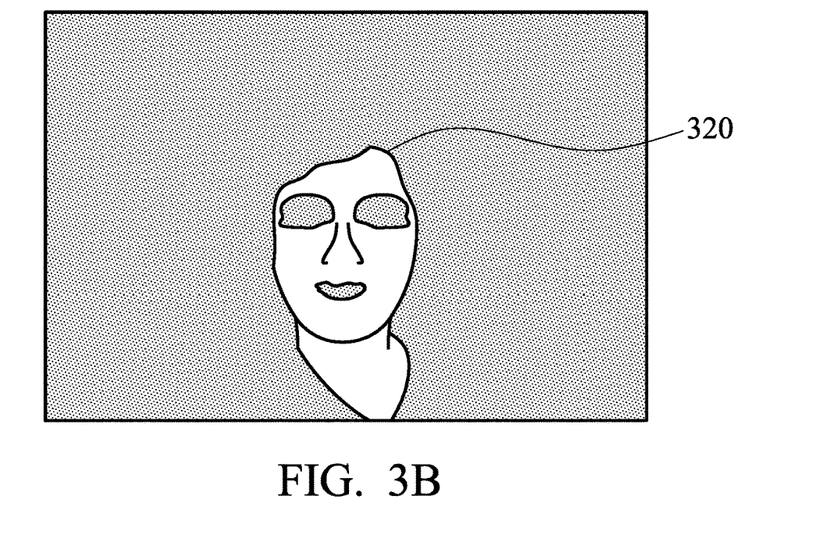
FIG. 3B is a schematic diagram illustrating an embodiment of the result of the skin color detection and retrieval of the invention.
Figure 3C:
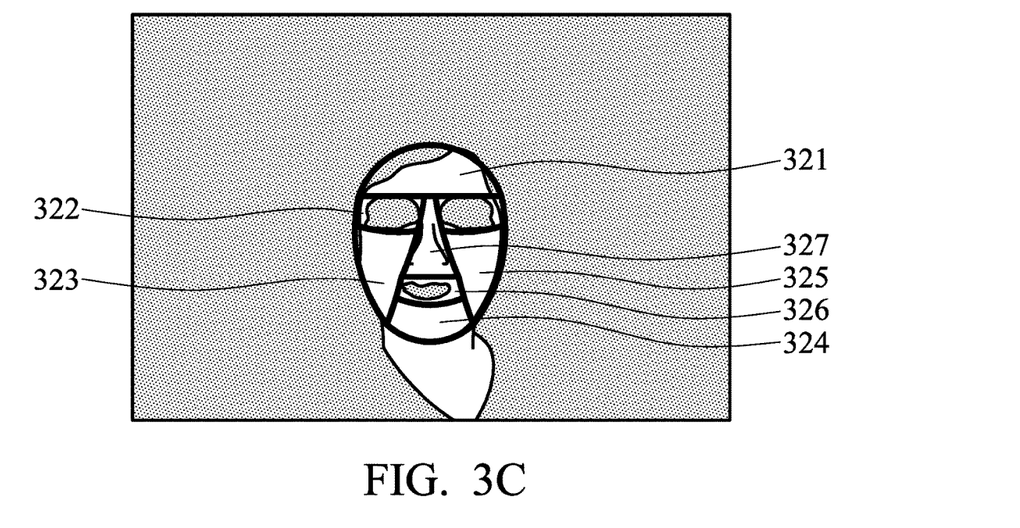
FIG. 3C is a schematic diagram illustrating an embodiment of the rough segmentation result of the face region of the invention.

To be more specific, the image processor 120 may first detect the face image in the image frame and based on the face feature points, perform face skin extraction to extract the skin location from the detected face image, and then divides the skin location of the face image into several large face regions, such as based on the face feature points, the face image is first divided into seven face regions including regions of the forehead, left cheek, right cheek, eyes, nose, chin and other, wherein these face features can be trained and obtained in advance, as shown in FIG. 3B and FIG. 3C. FIG. 3B is a schematic diagram illustrating an embodiment of the result of the skin color detection and retrieval of the invention. FIG. 3C is a schematic diagram illustrating an embodiment of the rough segmentation result of the face region of the invention. As shown in FIG. 3B and FIG. 3C, the skin color detection and retrieval result 320 is divided into the face regions 321 to 327 according to the face feature points.

Figure 4A:
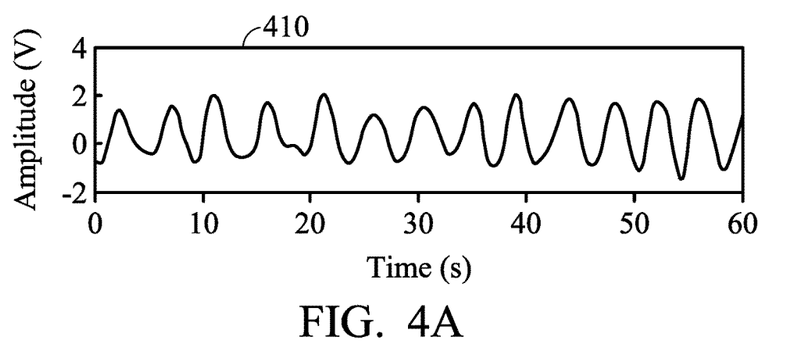
FIGS. 4A, 4B, and 4C are schematic diagrams illustrating an embodiment of the PPG information of the face region of the invention.
Figure 4B:
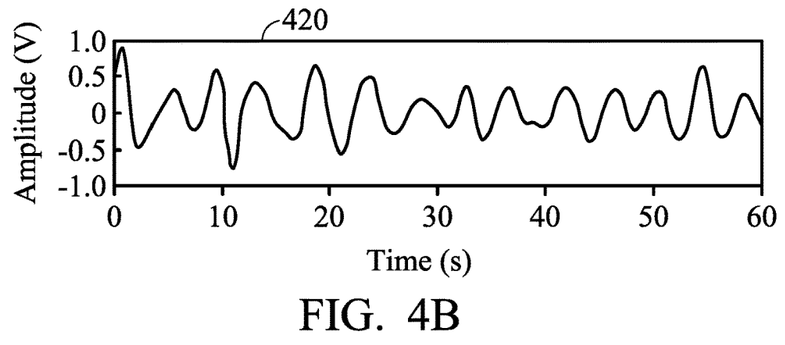
Figure 4C:
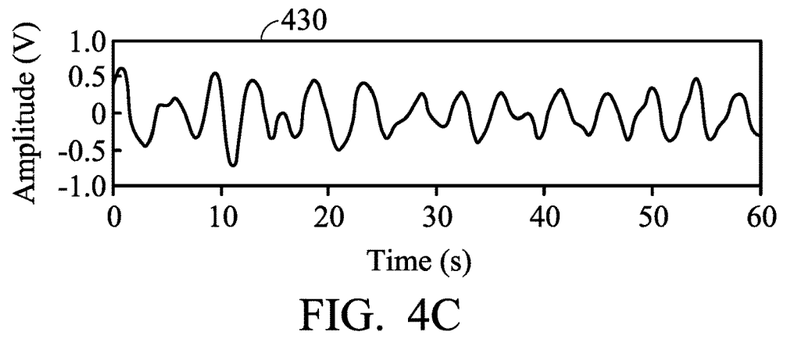

In one embodiment, the step that the image processor 120 performs the PPG calculation and analysis on each first region to obtain the first PPG information corresponding to the ROI may further include the steps of performing a pulse detection (also referred to as pulse measurement) algorithm on each of the first regions to perform the PPG calculation and analysis so as to obtain the first PPG information of each first region. It should be noted that details of specific pulse detection algorithms may be practiced by various pulse detection processing techniques which are well-known by those skilled in the art, and thus such details are omitted here for brevity. For example, in one embodiment, the image processor 120 may perform an Independent Component Analysis (hereinafter referred to as the ICA) calculation on each of the face regions 321 to 327 using the ICA algorithm to calculate the ICA waveform of the PPG signal for each of the face regions 321 to 327, compare the ICA waveforms of the face regions 321 to 327 with the waveform of a standard heartbeat to find the most matched ICA waveform, and then sets the face region (e.g., the forehead frontal region) corresponding to the most matched ICA waveform as ROI. The ICA can separate the PPG signal, noise and other independent components from original signals containing motion interference, select the independent component containing the PPG signal, and analyze the location of the PPG signal component with the independent component in the spectrum to achieve a goal for eliminating the motion interference. In one embodiment, the step that the image processor 120 determines the reserved region from the regions of face image according to the results of comparing the first PPG information and the threshold value may further comprise the step of comparing the first PPG information of each of the first regions with a first threshold value T2, and setting the first regions whose first PPG information are within a range of the first threshold value T2 as the reserved region. That is, only the first region whose PPG value is within the threshold value T2 is reserved as the ROI. For example, if the heartbeat is normal for 60 to 100 per minute, the threshold value T2 can be set to 1 to 1.6 per second and the face region (e.g., the forehead frontal region) whose heartbeat frequency or pulse signal represented by the PPG signal is kept between 1 to 1.6 per second can be reserved as a reserved region, but this invention is not limited thereto. FIGS. 4A to 4C are schematic diagrams illustrating an embodiment of the PPG information of the face region of the invention. It is assumed that the PPG information 410 and 420 of the face regions 321 and 322 are shown in FIG. 4A and FIG. 4B, respectively, and the PPG information 430 of the waveform of the standard heartbeat signal is shown in FIG. 4C. As can be seen from FIG. 4A, FIG. 4B and FIG. 4C, the PPG information 420 of the face region 322 is most matched to the PPG information 430 of the standard heartbeat signal, so that the image processor 120 may determine that the face region 322 is a reserved region and determine that the face region 321 is not a reserved region. After finding the reserved regions, the image processor 120 then subdivisions each reserved region into a plurality of smaller second regions, calculates the PPGs of these second regions, respectively, and then based on the second PPG information of the second regions of the reserved region, sets the second region whose second PPG information is within the range of the threshold value as the ROI and determine the noise reference region from the second regions whose second PPG information are not within the range of the threshold value. In some embodiments, the step of determining the noise reference region from the second regions whose second PPG information are not within the range of the second threshold value may further comprise the steps of performing a variance calculation on all the second regions whose second PPG information are not within the range of the threshold value to obtain a plurality of variance values and determining the noise reference region based on the variance values, wherein the noise reference region is a second region having the minimum variation value among the second regions whose second PPG information are not within the range of the threshold value.

After determining the ROI and the noise reference region of the first face image, as shown in step S208, the image processor 120 generates an ROI information and a noise reference region information based on the PPG calculation and analysis result for the ROI and the noise reference region of the first face image, wherein the ROI information includes location information and the PPG information corresponding to the ROI and the noise reference region information includes location information and the PPG information corresponding to the noise reference region. ROI information can include coordinates, pixels, PPG values and other information in the image for the ROI. The ROI here represents a more reliable region, meaning that the PPG values within the ROI are trustworthy, but are still likely to be affected by background noise. In contrast, the noise reference region is the region with the smallest variance value in all the regions within the image. The PPG value of the noise reference region can be regarded as background noise and should be removed for denoising. The noise reference region information may include information such as coordinates, pixels, PPG values, etc. in the region whose variance value is smallest in the regions of the image.

Specifically, after determining the ROI, the image processor 120 generates the ROI information and the noise reference region information based on the location information and the PPG signal corresponding to the ROI. The image processor 120 may then further calculate variance values for all the regions where the PPG value falls outside the threshold value T2, where the smaller the variance value calculated in a region, the smaller the gray scale change in the region and the more flat the region. The image processor 120 can compare the variance values of all regions where the PPG value falls outside the threshold value T2, set the region having the smallest variance value (e.g. the left cheek) as the noise reference region and record coordinates location in the image, PPG value and other information for the first region within the noise reference region to generate the noise reference region information. The noise reference region information is stored in the storage device 130, and then it can be used in subsequent background noise determination to perform the denoising process.

After generating the ROI information and the noise reference region information of the first face image, as shown in step S210, the image processor 120 then performs the PPG calculation and analysis on the ROI and the noise reference region of the second face image of each of the second image frames and generates corresponding PPG information based on the ROI information and the noise reference region information. In this step, the image processor 120 checks whether the ROI information and the noise reference region information already exist in the storage device 130. If there has the ROI information, it means that current image frame may be the image frame (e.g., the second image frame) following the first image frame, and thus the image processor 120 may directly perform the PPG calculation and analysis on the ROI of the current image frame according to the ROI information of the first image frame to obtain PPG signal corresponding to the ROI of the current image frame so as to generate aforementioned ROI information and noise reference region information. The image processor 120 may sequentially perform the PPG calculation and analysis on the ROI of each subsequent image frame according to the ROI information to obtain a PPG signal corresponding to its ROI and generate the ROI information and the noise reference region information.

Figure 5:
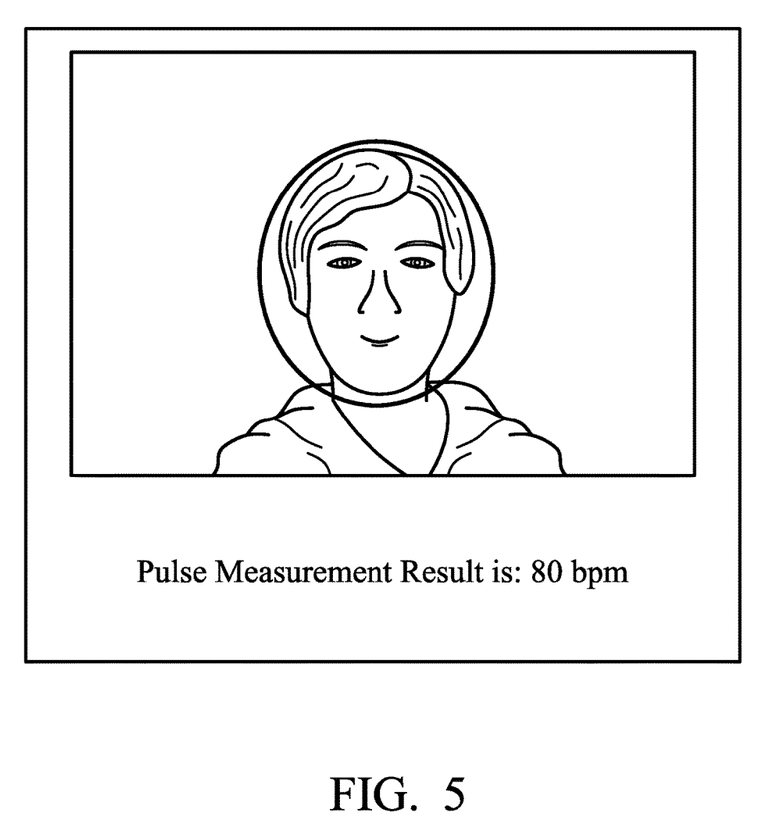
FIG. 5 is a schematic diagram illustrating an embodiment of the results of a pulse measurement of the invention.

After obtaining the PPG information of all the image frames, as shown in step S212, the image processor 120 counts the PPG information of all the image frames to calculate the measured value of a physiological signal, such as the measured value for the heart rate or the pulse measurement. Since the heart rate and the pulse must continue to count the PPG changes for a period of time in order to be successfully measured, the image processor 120 must accumulate image changes over a period of time. For example, the image processor 120 may perform peak detection of the PPG signal to detect the number of peaks for the PPG signal of each image frame and calculate an average of the number of peaks of all the image frames in order to produce the measured value of a physiological signal such as heart rate or pulse measurement. At the time of peak detection, the image processor 120 may calculate the slope of each time point in the skin color change waveform of the PPG signal to detect the peak occurrence time and the number of peaks, and after finding the positions of two peaks, a peak to peak interval (PPI) can be calculated. The heart rate value can be determined as the reciprocal of the PPI. The image processor 120 may present the measurement result of the physiological signal, such as heart rate or pulse, through the display device 140. FIG. 5 is a schematic diagram illustrating an embodiment of the results of a pulse measurement of the invention. As shown in FIG. 5, the result of pulse measurement is 80 beats per minute (bpm) in this embodiment.

In other embodiments, as the still user may actually have slightly movement, the present invention further provides a motion detection and exclusion mechanism to solve the problem of slightly movement in detection. In this embodiment, if the current image is the first image frame, there is no problem of user movement, and thus the image processor 120 does not perform the detection of the user movement. If the user has moved or a certain length of the video have been processed, the image processor 120 restarts recording the entire video and sets next image as the first image frame. Specifically, in a case where the user has no displacement and enough number of images has not yet accumulated, when processing the next image, the image processor 120 first determines whether the currently processed image frame is the first frame. If the currently processed image frame is not the first image frame (for example, currently processed image frame is the second image frame), the face detection of the second image frame is performed, and then the position and the size of the user's face of the image within the currently processed image frame are calculated and compared with those results detected by the previous image frame to determine the difference therebetween, and then whether the difference has exceeded the threshold value (e.g., the threshold value T1 is set to 0) is further determined. If the difference between the face position and the face size of the two image frames exceeds the threshold value T1, it indicates that the user's face has a movement (for example, the user's face has a left or right displacement or has been zoom-in or zoom-out with a distance), and thus entire video segment must be recaptured. On the other hand, if the difference between the face position and the face size of the two image frames is smaller than the threshold value, it means that the user's face is stationary, the PPG value of the image frame can be obtained and the background noise can be determined in the ROI of the currently processed image frame and the length of the video is continuously accumulated. By doing so, the image processor 120 does not need to perform face feature extraction and segmentation on each image frame to find a region where the PPG response is noticeable, thereby greatly reducing the amount of calculation needed.

Figure 6A:
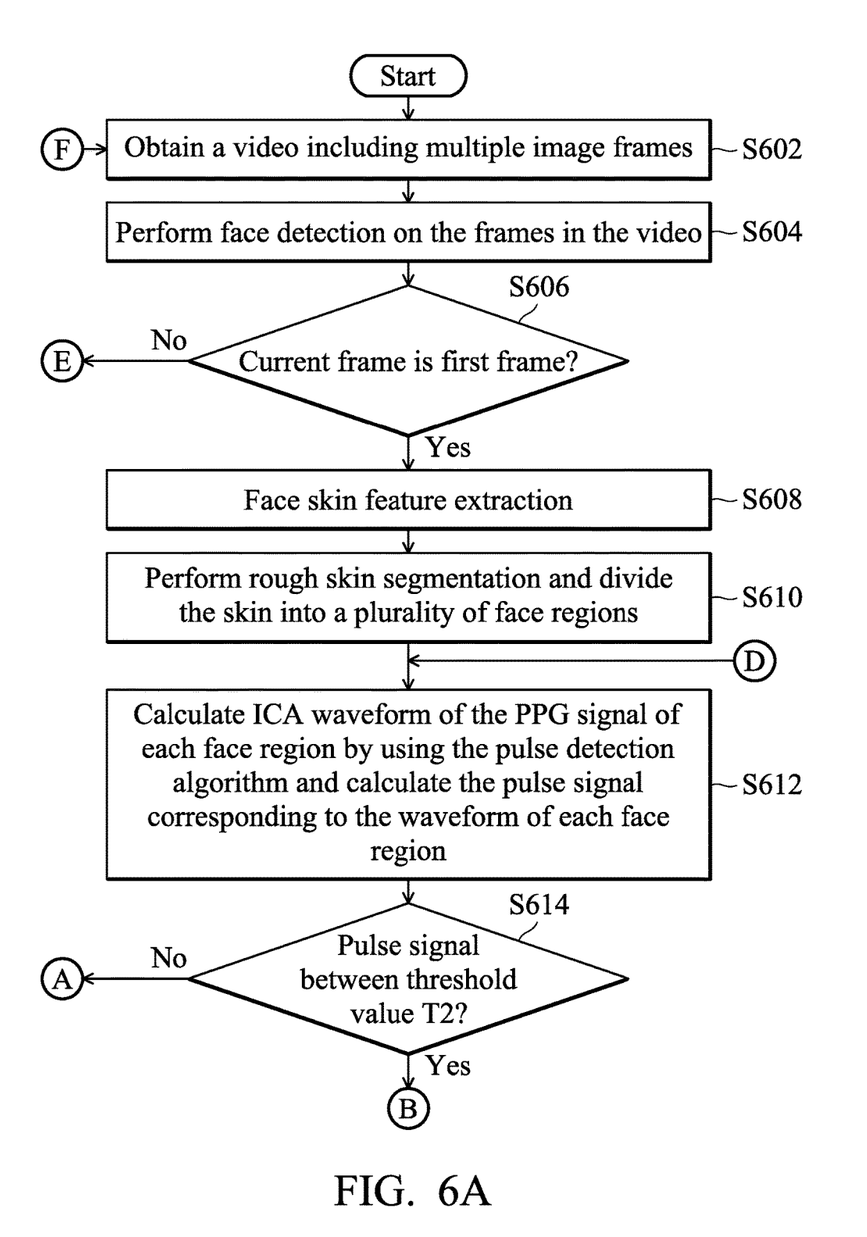
FIGS. 6A, 6B, and 6C show a flow chart of another embodiment of a method of for measuring the physiological signal of the invention.
Figure 6B:
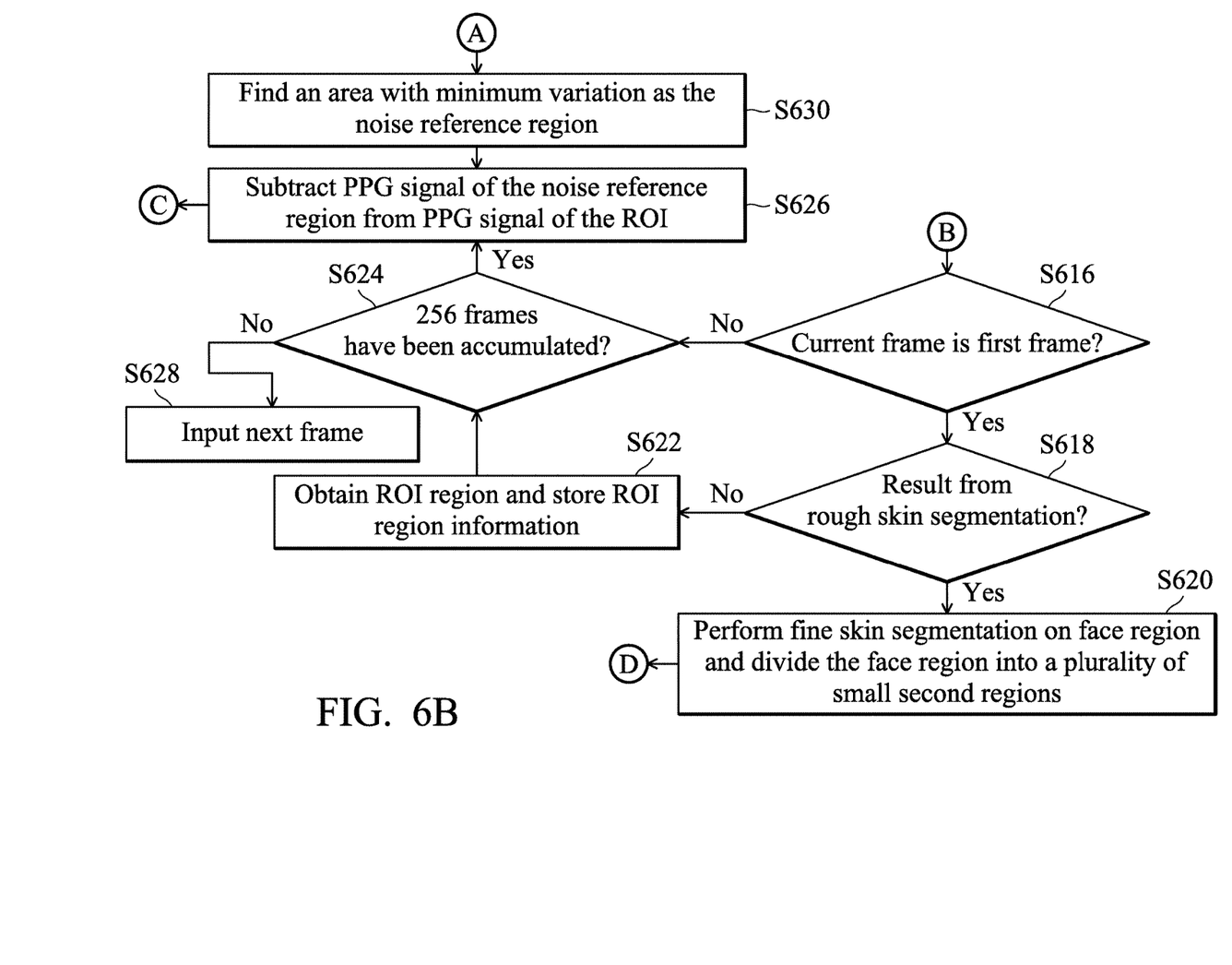
Figure 6C:
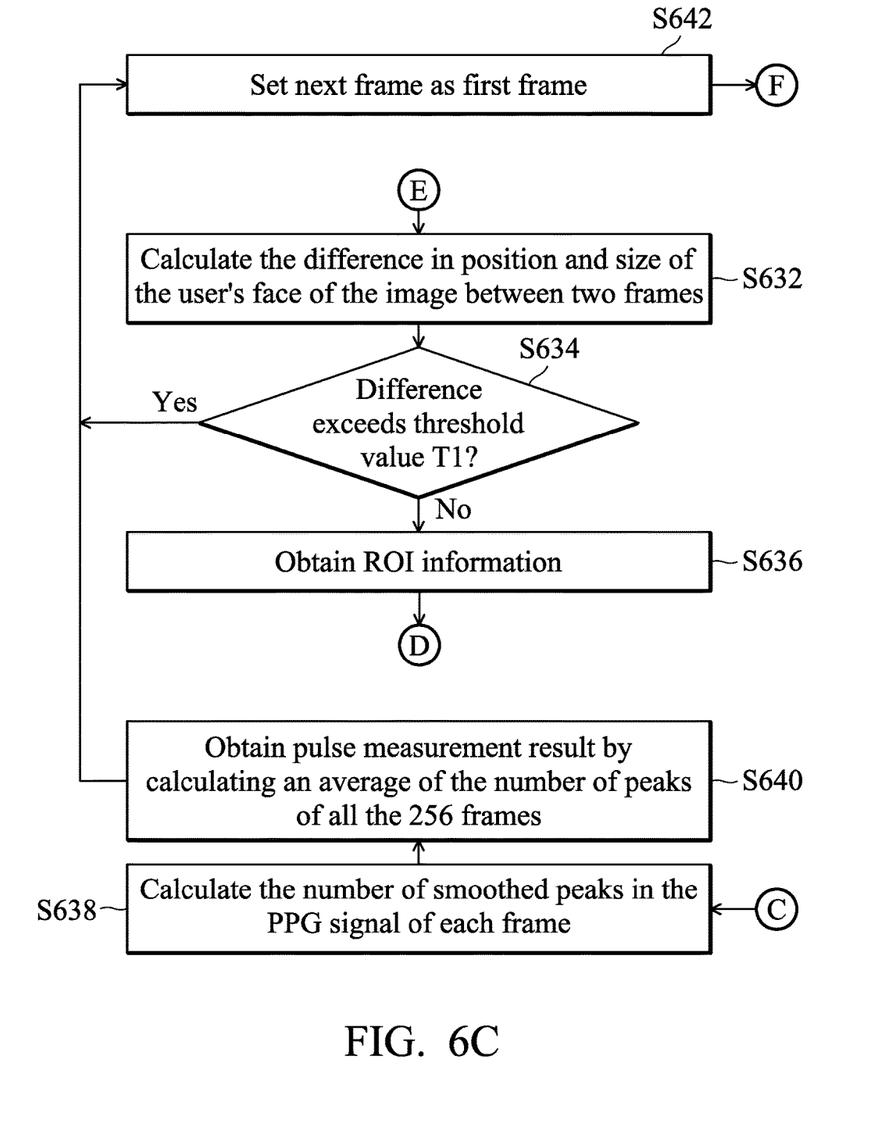

FIGS. 6A, 6B, and 6C together show a flow chart of another embodiment of a method for measuring the physiological signal of the invention. Please refer together with FIG. 1 and FIG. 6A to 6C. The method for measuring a physiological signal in accordance with the embodiments of the invention may be applied to a physiological signal measurement system, for example, the physiological signal measurement system 100 as shown in FIG. 1, and the method may be performed by the image processor 120.

In this embodiment, the image processor 120 first captures/obtains a video including multiple image frames (step S602) and performs face detection on the image frames in the video to obtain face images (step S604), such as the face image 310 shown in FIG. 3A. In this step, the image processor 120 must take a certain length (e.g., 256 frames) of a video segment from the full video accumulatively captured by the image processor 120 for subsequent PPG analysis.

Next, the image processor 120 performs the first image frame (first frame) determination in the received video to determine whether current image frame is the first image frame (step S606). Step S606 is to determine whether the image currently being processed is the first image frame in the video. If the current image frame is the first image frame (Yes in step S606), the image processor 120 continues to perform the ROI extraction to segment and extract the ROI from multiple face feature regions, where the ROI is the face feature region where the face PPG change is noticeable. If the current image frame is not the first image frame (No in step S606), the image processor 120 performs PPG detection on each of subsequent images using the location of the face feature region where the face PPG change is noticeable (i.e., the ROI position) for the first image frame.

During the ROI extraction, the image processor 120 performs face skin extraction to capture the position of the skin from the detected face image (step S608), and then performs rough skin segmentation to divide the skin into a plurality of large face regions (first regions) (step S610). Thereafter, the image processor 120 calculates the ICA waveform of the PPG signal of each face region and calculates the pulse signal corresponding to the waveform of each face region by using the pulse detection algorithm (step S612), and determines whether the pulse signal is between the threshold values T2 (step S614). Specifically, the image processor 120 may perform a pulse detection algorithm on each of the first regions to obtain a corresponding PPG value and only keep the first region whose PPG value is within the threshold value T2 (pulse between T2), wherein for all the first region whose PPG value is not within the threshold value, the image processor 120 may calculate the variance values for those first regions and find a first region with the minimum variance value and then store it, which can later be used to determine the background noise for noise reduction. The image processor 120 may achieve the purpose of noise reduction by subtracting the PPG value of the corresponding point of the region with the minimum variance value from the PPG value of each point for the ROI.

Figure 3D:
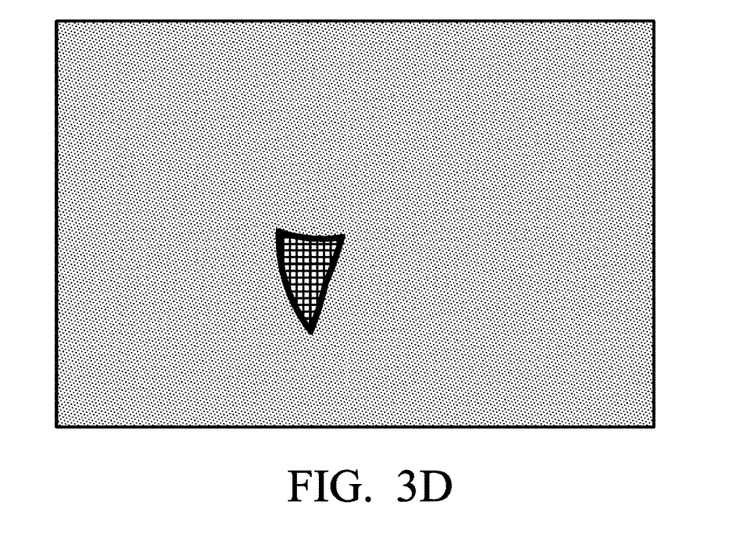
FIG. 3D is a schematic diagram illustrating an embodiment of the fine segmentation result of the face region of the invention.

Next, the image processor 120 determines whether the region reserved in the previous step corresponds to the first frame (step S616) or whether the previous step performed is rough skin segmentation (step S618), and if both answers are Yes, continues to perform fine skin segmentation on face region and divide the face region into a plurality of small second regions (step S620), as shown in FIG. 3D. Then, the image processor 120 again uses the pulse detection algorithm to calculate the ICA waveform of the PPG signal for each small second region and calculates the pulse signal corresponding to the waveform of each second region (step S612), and only reserves the second region whose PPG value is within the range of the threshold value T2, the second region being reserved is the ROI, and stores information regarding the coordinates, the pixels, the PPG value and so on in the image for the ROI. For the second regions whose PPG value are outside the threshold value T2, the variance values for such second regions are calculated and the region with the minimum variation is found as the noise reference region and stored (step S630).

If it is determined in step S618 that the previous step is not the rough segmentation, which indicates that the fine skin segmentation of step S620 has been performed and the reserved region is set as the ROI, the image processor 120 performs a pulse detection calculation on each of the second regions, the image processor 120 stores information regarding the coordinates, the pixels, the PPG value and so on in the image for the ROI (step S622).

If it is determined in step S616 that the current image frame is not the first image frame (No in step S616) or if the ROI information has already been stored, which means that the ROI information has been obtained and the ROI information can be used to obtain the PPG information corresponding to the ROI in each image frame, the image processor 120 then determines whether 256 image frames have been accumulated (step S624). If the number of the image frames being processed has not yet accumulated to 256 image frames (No in step S624), the image processor 120 captures/inputs next image frame from the video (step S628) and continues to use the ROI information to obtain the PPG information corresponding to the ROI in each image frame until it accumulates up to 256 image frames. If a total of 256 image frames have been accumulated (No in step S624), the image processor 120 subtracts the PPG signal value stored in the noise reference region stored in step S630 from the PPG signal value of the ROI (step S626), and then calculates the heart rate and pulse, by first calculating the number of smoothed peaks in the PPG signal of each image frame (calculate smoothed peak number) (step S638) and finally obtaining the pulse measurement result by calculating an average of the number of peaks of all the 256 frames (step S640).

If it is determined in step S606 that the currently processed image frame is the first image frame (Yes in step S606), the image processor 120 does not perform the detection of the user's movement in steps S632 to S634. On the contrary, if it is determined in step S606 that the currently processed image frame is not the first image frame (in this embodiment, it is assumed that the currently processed image frame is the second image frame), the image processor 120 then performs step S632 to step S634. During the detection of the user's movement, the image processor 120 first performs the face detection of the second image frame, and then calculates the difference in position and size of the user's face of the image between the currently processed image frame and previously image frame detected (calculate diff of face position & size) (step S632), and it is determined whether the difference exceeds the threshold value T1 (for example, the threshold value T1 is set to 0) (step S634). If the difference between the face position and the size of the two image frames exceeds the threshold value, for example, if the difference in the face position is greater than 0, which means that the user's face is moved (for example, the user's face has a left or right displacement or it has been zoom-in or zoom-out with a distance), entire video segment must be recaptured. On the other hand, if the difference between the face position and the size of the two image frames is smaller than the threshold value T1, it means that the user's face is stationary, the ROI information of the previous image frame (i.e., the first image frame) can be obtained (step S636) and the obtained ROI information can be used to obtain the PPG value of the image frame in the ROI of the currently processed image frame and determine the background noise in the ROI of the currently processed image frame and the length of the video is continuously accumulated. If the user has moved or a certain length of the video have been processed, the image processor 120 restarts receiving another entire accumulated video and sets the next image as the first image frame to reobtain the ROI information and the noise reference region information (step S642).

Therefore, according to the physiological signal measurement systems and methods for measuring a physiological signal thereof of the present invention, information pertaining to ROIs can be first obtained and subsequent images only require determining the user's face is in a stable state and directly obtaining PPG values from the ROIs after obtaining the ROI, without needing tracking or determining which regions are reliable, which is suitable for embedded systems and other systems with fewer computing resources and also reduce the data amount required to be processed during physiological signal detection calculation processes, thereby effectively resolving the problem of greater amount of calculations in the prior art. Furthermore, according to the physiological signal measurement systems and methods for measuring a physiological signal thereof of the present invention, the regions with less obvious face PPG changes can be used to determine background noise and denoise, thus further enhancing physiological signal measurement accuracy.

Systems and method thereof, or certain aspects or portions thereof, may take the form of a program code (i.e., executable instructions) embodied in tangible media, such as floppy diskettes, CD-ROMS, hard drives, or any other machine-readable storage medium, wherein, when the program code is loaded into and executed by a machine, such as a computer, the machine thereby becomes an apparatus for practicing the methods. The methods may also be embodied in the form of a program code transmitted over some transmission medium, such as electrical wiring or cabling, through fiber optics, or via any other form of transmission, wherein, when the program code is received and loaded into and executed by a machine, such as a computer, the machine becomes an apparatus for practicing the disclosed methods. When implemented on a general-purpose processor, the program code combines with the processor to provide a unique apparatus that operates analogously to application specific logic circuits.

While the invention has been described by way of example and in terms of preferred embodiment, it is to be understood that the invention is not limited thereto. Those who are skilled in this technology can still make various alterations and modifications without departing from the scope and spirit of this invention. Therefore, the scope of the present invention shall be defined and protected by the following claims and their equivalents.

What is claimed is:

1. A method for measuring a physiological signal, comprising:
receiving a video including a plurality of continuous image frames and performing face detection on each of the image frames to obtain a face image for each image frame, wherein the continuous image frames include a first image frame and a plurality of second image frames, and wherein the first image frame includes a first face image having first regions, each of the first regions having a plurality of second regions corresponding thereto;
performing a photo-plethysmography (PPG) calculation and analysis on the first face image of the first image frame to obtain a plurality of first PPG information of the first regions and a plurality of second PPG information of corresponding second regions;
determining a reserved region from the first regions according to the first PPG information of the first regions and a first threshold value, and determining at least one region-of-interest (ROI) and a noise reference region according to results of comparing the second PPG information of corresponding second regions for the reserved region and a second threshold value;
generating an ROI information and a noise reference region information based on the at least one ROI and the noise reference region of the first face image, wherein the ROI information includes location information and the PPG information corresponding to the at least one ROI and the noise reference region information includes location information and the PPG information corresponding to the noise reference region;
performing the PPG calculation and analysis on the ROI and the noise reference region of each second face image of each of the second image frames and generating corresponding third PPG information based on the ROI information and the noise reference region information; and
counting the PPG information of all the image frames to calculate a measured value of the physiological signal.

2. The method for measuring the physiological signal of claim 1, further comprising:
performing a rough skin segmentation on skin portion of the first face image according to face feature points to divide the first face image into the first regions.

3. The method for measuring the physiological signal of claim 1, wherein the step of determining the reserved region from the first regions according to the first PPG information of the first regions and the first threshold value further comprises:
comparing the first PPG information of each of the first regions with the first threshold value; and
setting one of the first regions whose first PPG information is within a range of the first threshold value as the reserved region.

4. The method for measuring the physiological signal of claim 3, wherein the step of determining the at least one ROI and the noise reference region according to the results of comparing the second PPG information of corresponding second regions for the reserved region and the second threshold value further comprises:
comparing the second PPG information of each of the second regions with the second threshold value; and
setting one of the second regions whose second PPG information is within a range of the second threshold value as the at least one ROI and determining the noise reference region from the second regions whose second PPG information are not within the range of the second threshold value.

5. The method for measuring the physiological signal of claim 4, wherein the step of determining the noise reference region from the second regions whose second PPG information are not within the range of the second threshold value further comprises:
performing a variance calculation on all the second regions whose second PPG information are not within the range of the second threshold value to obtain a plurality of variance values; and
determining the noise reference region based on the variance values;
wherein the noise reference region is a second region having the minimum variation value among the second regions whose second PPG information are not within the range of the second threshold value.

6. The method for measuring the physiological signal of claim 1, wherein the step of performing the PPG calculation and analysis on the first face image of the first image frame to obtain the first PPG information of the first regions and the second PPG information of corresponding second regions further comprises:
performing a pulse detection algorithm on each of the first regions and the corresponding second regions to perform the PPG calculation and analysis to obtain the first PPG information of the first region and the second PPG information of corresponding second regions.

7. The method for measuring the physiological signal of claim 1, further comprising:
performing the face detection to calculate a difference in the face position and size between currently processed image frame and a previously processed image frame;
directly performing the PPG calculation and analysis on the ROI of the currently processed image frame and obtaining the PPG information of the currently processed image frame based on the PPG calculation result when the difference is not greater than a threshold value; and
setting the currently processed image frame as the first image frame to redefine the ROI and the noise reference region when the difference is greater than the threshold value.

8. A physiological signal measurement system, comprising:
an image input device, configured to obtain a video including a plurality of continuous image frames, wherein the continuous image frames include a first image frame and a plurality of second image frames, and wherein the first image frame includes a first face image having first regions, each of the first regions having a plurality of second regions corresponding thereto;
an image processor coupled to the image input device, configured to receive the video and perform face detection on each of the image frames to obtain a face image for each image frame, perform a photo-plethysmography (PPG) calculation and analysis on the first face image of the first image frame to obtain a plurality of first PPG information of the first regions and a plurality of second PPG information of the corresponding second regions, determine a reserved region from the first regions according to the first PPG information of the first regions and a first threshold value, determines at least one region-of-interest (ROI) and a noise reference region according to results of comparing the second PPG information of corresponding second regions for the reserved region and a second threshold value, generate an ROI information and a noise reference region information based on the at least one ROI and the noise reference region of the first face image, wherein the ROI information includes location information and the PPG information corresponding to the at least one ROI and the noise reference region information includes location information and the PPG information corresponding to the noise reference region, perform the PPG calculation and analysis on the ROI and the noise reference region of each second face image of each of the second image frames and generate corresponding third PPG information based on the ROI information and the noise reference region information, and count the PPG information of all the image frames to calculate a measured value of a physiological signal; and a display device coupled to the image processor, configured to display the measured value of the physiological signal.

9. The physiological signal measurement system of claim 8, wherein the image processor further performs a rough skin segmentation on skin portion of the first face image according to face feature points to divide the first face image into the first regions.

10. The physiological signal measurement system of claim 8, wherein the image processor further compares the first PPG information of each of the first regions with the first threshold value and sets one of the first regions whose first PPG information is within a range of the first threshold value as the reserved region.

11. The physiological signal measurement system of claim 10, wherein the image processor further compares the second PPG information of each of the second regions with the second threshold value, sets one of the second regions whose second PPG information is within a range of the second threshold value as the at least one ROI, and determines the noise reference region from the second regions whose second PPG information are not within the range of the second threshold value.

12. The physiological signal measurement system of claim 11, wherein the image processor further performs a variance calculation on all the second regions whose second PPG information are not within the range of the second threshold value to obtain a plurality of variance values and determines the noise reference region based on the variance values, wherein the image processor sets a second region having the minimum variation value among the second regions whose second PPG information are not within the range of the second threshold value as the noise reference region.

13. The physiological signal measurement system of claim 8, wherein the image processor performs a pulse detection algorithm on each of the first regions and the corresponding second regions to perform the PPG calculation and analysis to obtain the first PPG information of the first region and the second PPG information of corresponding second regions.

14. The physiological signal measurement system of claim 8, wherein the image processor further performs the face detection to calculate a difference in the face position and size between currently processed image frame and a previously processed image frame, directly performs the PPG calculation and analysis on the ROI of the currently processed image frame and obtain the PPG information of the currently processed image frame based on the PPG calculation result when the difference is not greater than a threshold value, and sets the currently processed image frame as the first image frame to redefine the ROI and the noise reference region when the difference is greater than the threshold value.

* * * * *